United States Patent [19]

Tiefenbrun et al.

[11] Patent Number: 5,375,608
[45] Date of Patent: Dec. 27, 1994

[54] METHOD AND INSTRUMENT ASSEMBLY FOR USE IN OBTAINING BIOPSY

[76] Inventors: Jonathan Tiefenbrun, 62 Country Rd., Mamaroneck, N.Y. 10543; Peter J. Wilk, 185 W. End Ave., New York, N.Y. 10023

[21] Appl. No.: 50,887

[22] Filed: Apr. 21, 1993

[51] Int. Cl.⁵ .............................................. A61B 10/00
[52] U.S. Cl. ...................................................... 128/754
[58] Field of Search .............................. 128/751–754, 128/760; 606/167, 170

[56] References Cited

U.S. PATENT DOCUMENTS

| | | | |
|---|---|---|---|
| 3,577,979 | 5/1971 | van der Gaast . | |
| 3,630,192 | 12/1971 | Janshidi . | |
| 4,142,517 | 3/1979 | Stauropoulos et al. . | |
| 4,249,541 | 2/1981 | Pratt | 128/753 |
| 4,427,014 | 1/1984 | Bel et al. | 128/751 |
| 4,580,577 | 4/1986 | O'Brien et al. | 128/760 |
| 4,651,752 | 3/1987 | Fuerst | 128/754 |
| 4,656,999 | 4/1987 | Storz | 128/751 |
| 4,781,202 | 11/1988 | Janese | 128/754 |
| 4,903,709 | 2/1990 | Skinner | 128/754 |
| 4,926,877 | 5/1990 | Bookwalter | 128/754 |
| 5,111,828 | 5/1992 | Kornberg et al. | 128/754 |
| 5,133,360 | 7/1992 | Spears | 128/754 |

FOREIGN PATENT DOCUMENTS 198770  4/1965  Sweden .............................. 128/754

*Primary Examiner*—Max Hindenburg
*Attorney, Agent, or Firm*—R. Neil Sudol; Henry D. Coleman

[57] ABSTRACT

A method for obtaining a biopsy uses an instrument assembly which includes an elongate tubular member having a distal end portion defining a specimen-receiving chamber, the instrument assembly being provided at a distal end with a cutting blade extending in a plane oriented substantially transversely with respect to the tubular member. The distal end portion of the tubular member is inserted into organic tissues of a patient so that some of the tissues enter the chamber. Upon sufficient insertion of the distal end portion of the tubular member into the organic tissues of the patient, the blade is moved in the transverse plane to thereby sever the tissues in the chamber from tissues outside the chamber. Upon shifting of the blade to sever the tissues in the specimen-receiving chamber, the distal end portion of the tubular member is removed from the patient, together with the severed tissue sample.

8 Claims, 3 Drawing Sheets

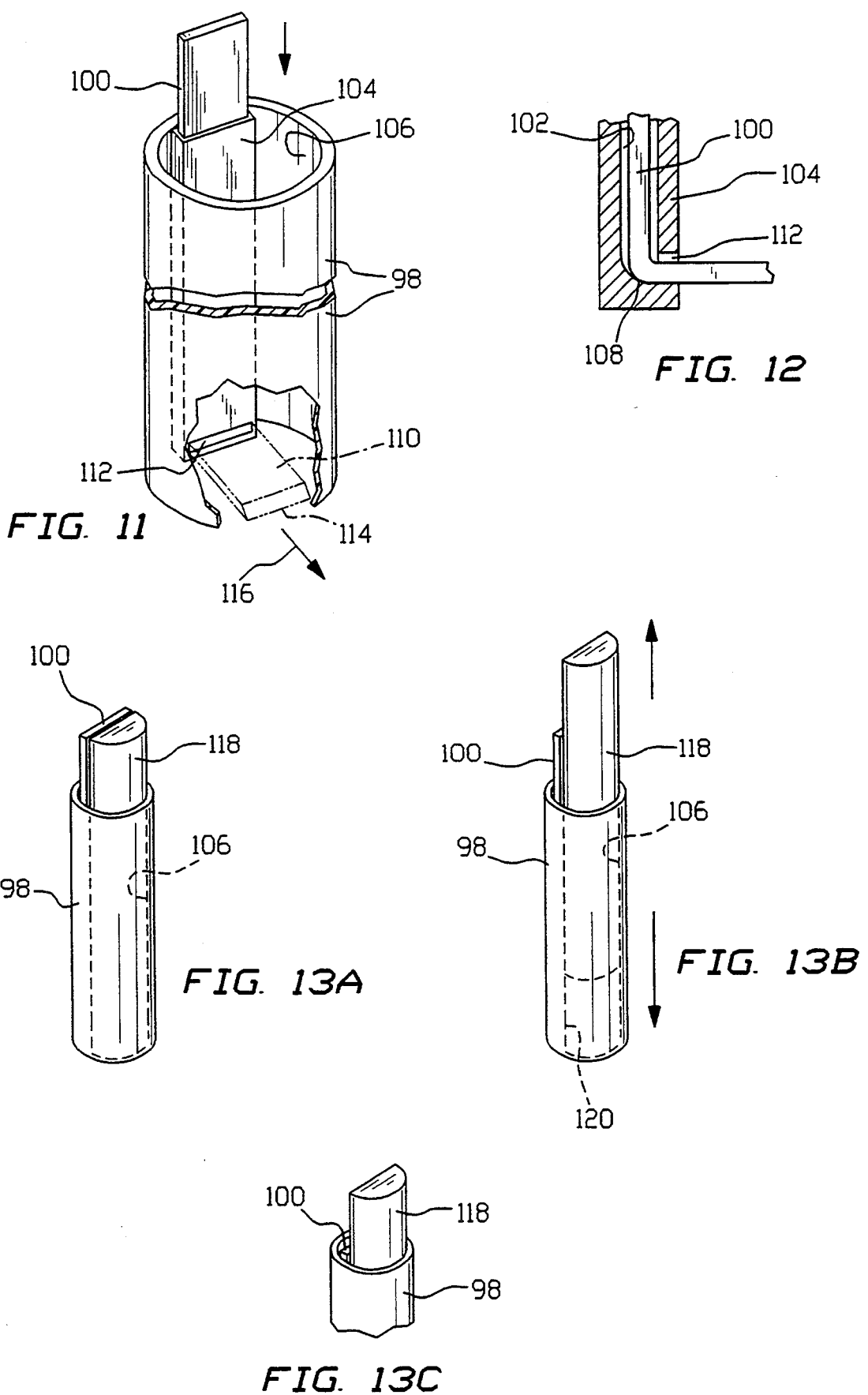

METHOD AND INSTRUMENT ASSEMBLY FOR USE IN OBTAINING BIOPSY

BACKGROUND OF THE INVENTION

This invention relates to a method for obtaining a biopsy. This invention also relates to an associated instrument assembly for use in obtaining a biopsy.

Vascular surgeons deal in part with venous disease. Venous disease arises, for example, in elderly patients with poor circulation. In such patients, the heart is not pumping adequately. As a result, ulcers are formed. The feet swell and the skin stretches. Moreover, ulcers can form in bone tissue.

The conventional procedure for obtaining a biopsy, for instance, from bone tissue, requires surgery. Overlying tissues of the patient are cut open, the subject tissues are carved to separate a specimen, and the specimen is grasped with a forceps and placed into a culture medium.

Inasmuch as the conventional procedure is surgery, it can entail many steps common to surgery. Anesthesia, operating room, assistants, nurses, and instrumentation all come into play. Accordingly, taking a biopsy can become quite involved.

OBJECTS OF THE INVENTION

An object of the present invention is to provide a simplified method for obtaining a biopsy.

Another object of the present invention is to provide such a method which may be used to obtain bone tissue specimens, at least in elderly patients.

Another, more particular, object of the present invention is to provide a biopsy technique which does not invariably require general anesthesia.

A further object of the present invention is to provide an instrument assembly for use in the method.

These and other objects of the present invention will be apparent from the drawings and detailed descriptions herein.

SUMMARY OF THE INVENTION

A method for use in obtaining a biopsy comprises, in accordance with the present invention, the step of providing an instrument assembly including an elongate tubular member having a distal end portion defining a specimen-receiving chamber, the instrument assembly being provided at a distal end with a cutting blade extending in a plane oriented substantially transversely with respect to the tubular member. The distal end portion of the tubular member is inserted into organic tissues of a patient so that some of the tissues enter the chamber. Upon sufficient insertion of the distal end portion of the tubular member into the organic tissues of the patient, i.e., upon entry of sufficient tissues into the chamber in the tubular member, the blade is moved in the transverse plane to thereby sever the tissues in the chamber from tissues outside the chamber. Upon shifting of the blade, i.e., upon the severing of the tissues in the specimen-receiving chamber, the distal end portion of the tubular member is removed from the patient, together with the severed tissue sample.

According to another feature of the present invention, where the blade is a linear blade extending diametrically across a distal end face of the tubular member, the blade is moved by rotating the blade in the transverse plane. More particularly, the blade may be fixed at opposite ends to the tubular member. In that case, the blade is rotated by rotating the tubular member.

In a specific embodiment of the present invention, the tubular member constitutes an inner tubular member of the instrument assembly. The instrument assembly further includes an outer tubular member surrounding the inner tubular member, the blade being fixed at opposite ends to the outer tubular member. In this embodiment, the outer tubular member is rotated relative to the inner tubular member.

In a different embodiment of the present invention, a rod rotatably traverses the tubular member, the blade being attached to a distal end of the rod. In this embodiment, rotating the rod results in a rotation of the blade.

According to another feature of the present invention, an obturator is slidably inserted in the tubular member. The obturator is maintained inserted in the tubular member during an initial part of an insertion stroke so that the obturator prevents entry of overlying tissues into the tubular member. Subsequently, the obturator is shifted in a proximal direction relative to the tubular member while the tubular member is maintained in the patient. Upon a shifting of the obturator relative to the tubular member, the tubular member is inserted further into the patient, thereby obtaining a specimen of underlying tissues, the blade is a linear blade extending diametrically across a distal end face of the tubular member, the step of moving including the step of rotating the blade in the plane.

Where the tubular member is provided with an obturator, the obturator may be pushed into the specimen chamber, upon removal of the instrument assembly from the patient, to eject severed organic tissues captured in the chamber. This procedure facilitates the preservation of the specimen for transportation to a testing laboratory. Alternatively, the specimen may be ejected by using a swab or other tool upon removal of the obturator from the tubular member.

According to a further feature of the present invention, the instrument assembly includes at least one culture medium in the tubular member. Thus, a collected specimen is automatically placed in contact with a culture medium without additional steps. The tubular member with the specimen may be transported to a laboratory. A cap may be placed over one or both ends of the tubular member to enclose and seal the specimen.

According to an additional feature of the present invention, the blade is linearly shifted in the transverse plane. For example, the blade may be provided at the end of a web which is pushed in a longitudinal direction along the tubular member and bent at a distal end to turn a distal end portion of the web from a longitudinal orientation to an orientation extending transversely with respect to the tubular member.

An instrument assembly for use in obtaining a biopsy comprises, in accordance with the present invention, an elongate tubular member defining a specimen-receiving chamber at a distal end and a cutting blade having a cutting edge extending in a plane oriented transversely with respect to the tubular member, the cutting blade being operatively connected to the tubular member.

Pursuant to another feature of the present invention, the blade is fixed at opposite ends to an edge of the tubular member. As mentioned above, an obturator may be inserted into the tubular member.

Pursuant to a further feature of the present invention, means are operatively connected to the blade and the tubular member for shifting the blade in a linear direction in the transverse plane. In one specific embodiment, the blade is provided at the end of a web which is slidably mounted to the tubular member. Means are provided on the tubular member for bending the web at a distal end of the tubular member during a longitudinal shifting of the web.

Pursuant to an additional feature of the present invention, the tubular member is a first tubular member and the instrument assembly further comprises a second tubular member coaxially surrounding the first tubular member. The blade is attached to the second tubular member at a distal end thereof, while the second tubular member is rotatable with respect to the first tubular member.

In an alternative embodiment of the invention, a rod rotatably traverses the tubular member, the blade being attached to a distal end of the rod.

Pursuant to yet another feature of the present invention, the instrument assembly further comprises at least one culture medium in the tubular member. Also, the tubular member may provided at the distal end with a sharp edge oriented distally for facilitating insertion of the tubular member into organic tissues a patient.

A method in accordance with the present invention represents a simplified procedure for obtaining a biopsy.

A method in accordance with the present invention may be used to obtain bone tissue specimens, at least in elderly patients.

BRIEF DESCRIPTION OF THE DRAWING

FIG. 11 is a schematic perspective view, on a greatly enlarged scale, of yet another instrument assembly in accordance with the present invention.

FIG. 12 is a partial cross-sectional view of a distal end of the instrument assembly of FIG. 11.

FIGS. 13A-13C are schematic perspective views of the instrument assembly of FIG. 11, showing successive steps in the use of the instrument assembly in taking a biopsy in accordance with the present invention.

DETAILED DESCRIPTION

Figure 1:
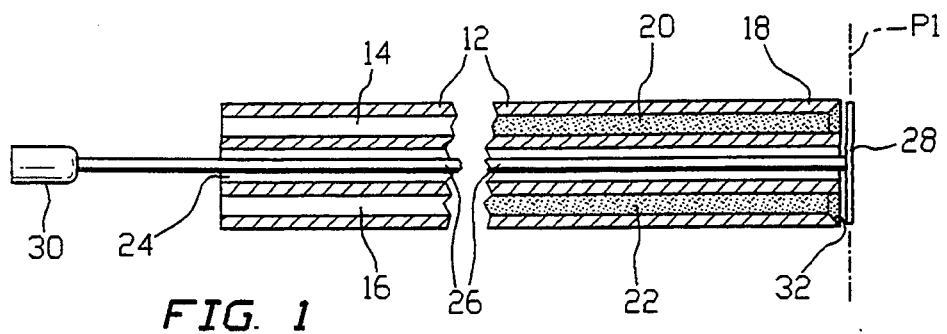
FIG. 1 is a schematic longitudinal cross-sectional view, on an enlarged scale, of a first embodiment of an instrument assembly for obtaining a biopsy, in accordance with the present invention.

As illustrated in FIG. 1, an instrument assembly for taking a biopsy, for example, of soft bone tissue, comprises a tubular member 12 provided with a pair of elongate channels or specimen-receiving chambers 14 and 16. Channels 14 and 16 are at least partially filled, particularly at the distal end 18 of the instrument assembly, with an aerobic culture medium 20 and an anaerobic culture medium 22, respectively. Tubular member 12 has another channel 24 longitudinally traversed by a rod 26 provided at a distal end with a transversely oriented blade member 28 extending in a plane P1 which is transversely oriented relative to tubular member 12. Rod 26 is rotatably inserted in channel 24, whereby blade member 28 may be turned in plane P1. The proximal end of rod 26 may be provided with a handle or grip 30 for facilitating the turning of rod 26 and blade member 28.

Tubular member 12 is beveled at distal end 18 to form a circular cutting edge 32 for facilitating the insertion of a distal end portion of tubular member 12 into organic tissues of a patient.

Figure 2:
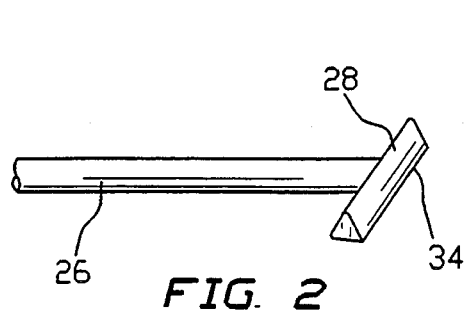
FIG. 2 is a partial perspective view of a component of the assembly of FIG. 1.

As illustrated in FIG. 2, blade member 28 has an elongate linear cutting edge 34. Edge 34 is oriented in plane P1 (FIG. 1) and is rotatable about an axis defined by rod 26.

In use, the distal end portion of tubular member 12 is inserted into organic tissues of a patient so that some of the tissues enter chambers or channels 14 and 16. Insertion is facilitated by the small diameter of tubular member 12, as well as by annular cutting edge 32. Upon entry into the distal ends of channels 14 and 16, the organic tissues come into contact with the respective culture medium 20 and 22.

Upon sufficient insertion of the distal end portion of tubular member 12 into the organic tissues of the patient, i.e., upon entry of sufficient tissues into channels 14 and 16, rod 26 is rotated to turn blade 28 in plane P1 and thereby sever the tissues inserted in channels 14 and 16 from tissues outside tubular member 12. Upon completing the turning of blade 28, i.e., upon the severing of the tissues in the specimen-receiving chambers or channels 14 and 16, the distal end portion of tubular member 12 is removed from the patient, together with the severed tissue samples.

At that juncture, handle 30 may be unscrewed from rod 26 and then rod 26 removed from channel 24. End caps (not illustrated) may be placed over the ends of tubular member 12, which can then be transported to a laboratory for testing of the captured specimens. Alternatively, as discussed in detail hereinafter with reference to FIGS. 9 and 10, obturators or other pushers may be inserted into channels 14 and 16 to force the specimens from the distal ends of the channels into transport and storage containers (not shown).

Figure 3:
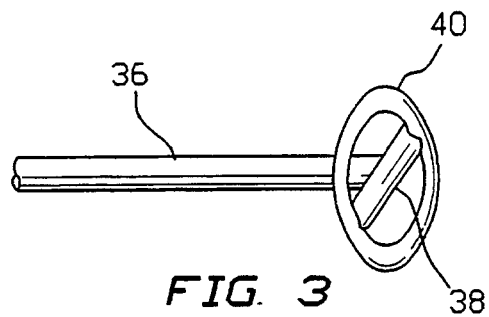
FIG. 3 is a partial schematic perspective view of an alternative form of the component of FIG. 2.

FIG. 3 depicts an alternative component for severing a tissue sample upon insertion of tubular member 12 into a patient. A rod 36 is provided at a free end with a blade member 38 which extends substantially orthogonally to the rod and which is connected at its free ends to an annular support 40. Blade member 38 extends diametrically with respect to support 40. Support 40 may be disposed in a recess or groove (see FIG. 5) in tubular member 12, the support riding in the recess or groove during rotation of rod 36 upon sufficient insertion of tubular member 12 into a patient.

It is to be noted that blade member 28 or 38 may be replaced by other equivalent blades. For example, more than two blade arms (not shown) may extend from the distal end of rod 26 or 36 at different angles.

Figure 4:
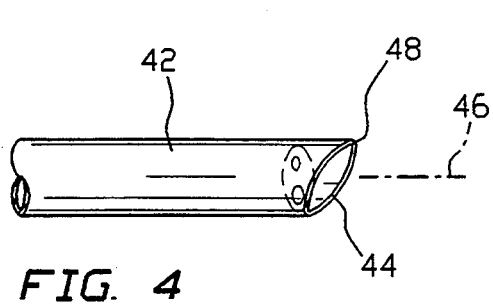
FIG. 4 is a partial schematic perspective view of a distal end of a modified biopsy instrument assembly in accordance with the present invention.

As illustrated in FIG. 4, a tubular member 42 of a biopsy instrument assembly may be beveled at a distal end to form a rim 44 at an angle with respect to a longitudinal axis 46 of tubular member 42. Rim 44 forms a pointed end 48 for facilitating insertion of tubular member 42 into a patient.

Figure 5:
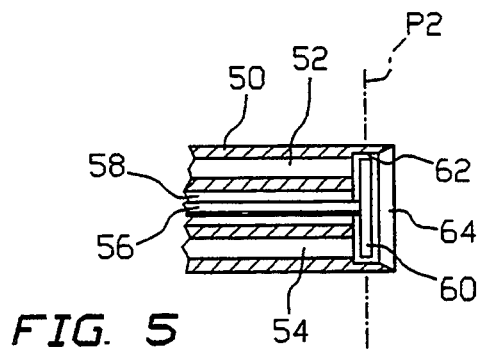
FIG. 5 is a partial schematic longitudinal cross-sectional view of another modified instrument assembly in accordance with the present invention.

As depicted in FIG. 5, a tubular member 50 of a biopsy instrument assembly is provided with a pair of specimen-receiving channels or chambers 52 and 54 and a rod 56 traversing another channel 58. Rod 56 is provided at a distal end with a blade member 60 which is seated in a recess 62 at the distal end of tubular member 50. A distal rim 64 of tubular member 50 is beveled to provide a cutting insertion edge. Blade member 60 is rotatable in a plane P2 which is oriented transversely to tubular member 50. The modified instrument assembly of FIG. 5 is used in the same way as the instrument assembly of FIG. 1.

Figure 7:
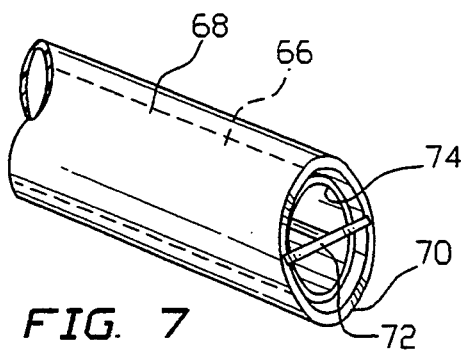
FIG. 7 is a partial schematic perspective view of the instrument assembly of FIG. 6.
Figure 6:
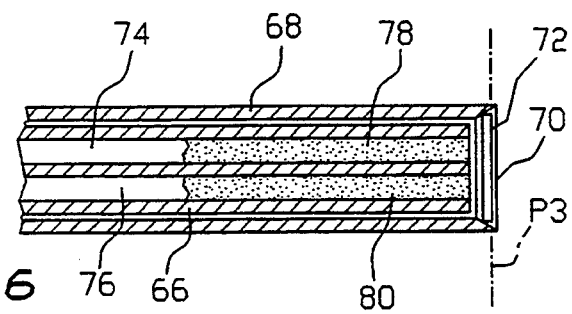
FIG. 6 is a partial schematic longitudinal cross-sectional view of another embodiment of an instrument assembly in accordance with the present invention.
Figure 8A:
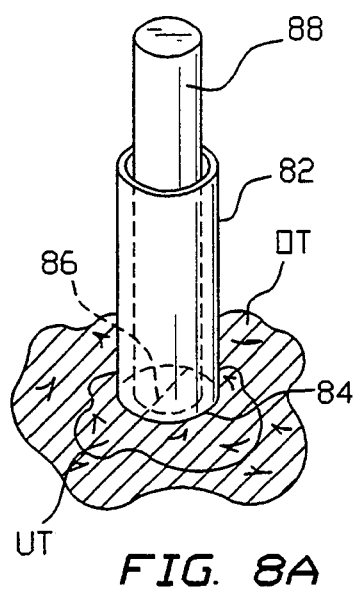
FIGS. 8A-8C are schematic perspective views of a further embodiment of an instrument assembly in accordance with the present invention, showing successive steps in the use of the instrument assembly in taking a biopsy in accordance with the present invention.
Figure 8B:
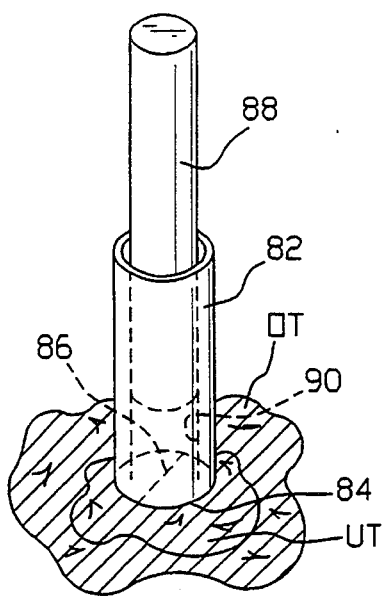
Figure 8C:
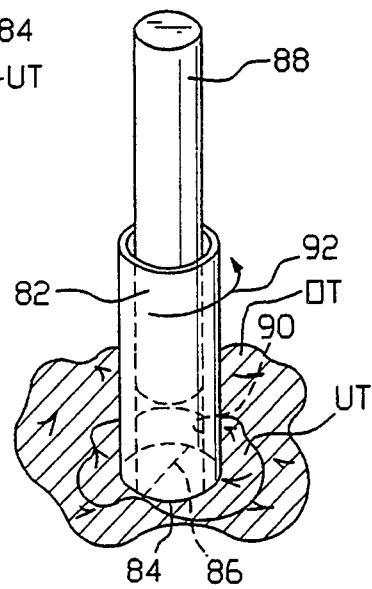

FIGS. 6 and 7 show another embodiment of a biopsy instrument assembly comprising an inner tubular member 66 and an outer tubular member 68 coaxially surrounding the inner tubular member 66. Outer tubular member 68 is formed at a distal end with a beveled edge 70 and a diametrically extending blade element 72. Inner tubular member 66 has a pair of specimen-receiving channels or chambers 74 and 76 which may be partially filled at a distal end with an aerobic culture medium 78 and an anaerobic culture medium 80, respectively.

In use, the distal end portions of tubular members 66 and 68 are inserted together into organic tissues of a patient so that some of the tissues enter chambers or channels 74 and 76. Insertion is facilitated by the small diameter of outer tubular member 68, as well as by annular cutting edge 70. Upon entry into the distal ends of channels 74 and 76, the organic tissues come into contact with the respective culture medium 78 and 80.

Upon sufficient insertion of the distal end portion of tubular members 66 and 68 into the organic tissues of the patient, i.e., upon entry of sufficient tissues into channels 74 and 76, outer tubular member 68 is rotated to turn blade 72 in a transversely extending plane P3 and thereby sever the tissues inserted in channels 74 and 76 from tissues outside tubular member 68. Upon completing the turning of blade 72, i.e., upon the severing of the tissues in the specimen-receiving chambers or channels 74 and 76, tubular members 66 and 68 are removed from the patient, together with the severed tissue samples.

At that juncture, inner tubular member 66 may be removed from outer tubular member 68 and covered with end caps (not shown). Alternatively the tissue specimens in channels 74 and 76 may be pushed out into respective storage and transport containers (not shown).

A simplified instrument assembly for use in obtaining a biopsy, particularly of underlying organic tissues UT, is illustrated in FIGS. 8A–8C and FIGS. 9 and 10. The instrument assembly includes a tubular member 82 provided at a distal end with a sharpened edge 84 and a diametrically extending blade element 86. An obturator 88 is slidably inserted into tubular member 82. During an initial step in a biopsy procedure, illustrated in FIG. 8A, tubular member 82 is inserted together with obturator 88 through tissues OT overlying the tissues UT of which a sample is desired. Obturator 88 occupies a channel 90 in tubular member 82 and thereby blocks insertion of overlying tissues OT during the initial step of the biopsy procedure.

Upon the arrival of the distal end of tubular member 82 at the region of underlying tissues UT, obturator 88 is withdrawn in the proximal direction (FIG. 8B), thereby opening a chamber at the distal end of channel 90. Tubular member 82 is then inserted further into the patient so that a specimen TS (FIGS. 9 and 10) of underlying tissues UT enters the distal end of channel 90. Upon completion of this insertion (FIG. 8C), tubular member 82 is twisted so that blade element 86 rotates (arrow 92) to sever the captured tissue specimen TS.

Figure 9:
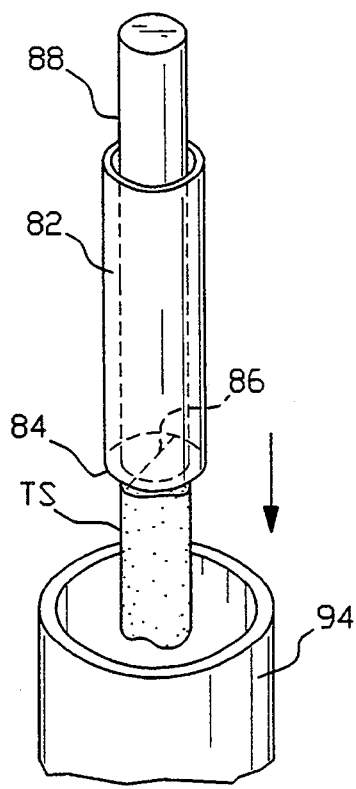
FIG. 9 is a schematic perspective view, showing a step subsequent to the steps depicted in FIGS. 8A-8C.
Figure 10:
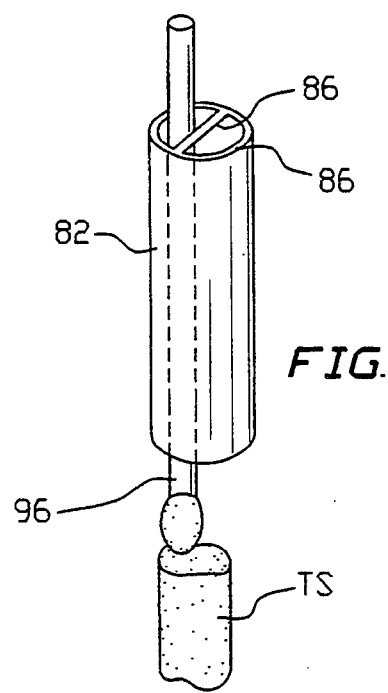
FIG. 10 is a schematic perspective view, showing an alternative step subsequent to the steps depicted in FIGS. 8A-8C.

Upon severing of tissue specimen TS from the remaining organic tissues of the patient, tubular member 82 is withdrawn. As illustrated in FIG. 9, obturator 88 may then be used to push tissue specimen TS from the distal end of tubular member 82 into a container 94 holding a culture medium (not shown). Alternatively, obturator 88 may be withdrawn (before or after the pressing of tubular member 82 into underlying tissues UT), whereupon a swab 96 or other elongate element is used to push tissue specimen TS from tubular member 82, as illustrated in FIG. 10.

It is to be noted that blade members 72 and 86 may take the form of fine wires.

As depicted in FIG. 11, another instrument assembly for use in obtaining a biopsy includes a tubular member 98 and an elongate rectangular web 100 slidably inserted through a narrow channel 102 of rectangular cross-section. Channel 102 is formed by a hollow prismatic guide member 104 secured to tubular member 98 along a channel 106 thereof. At a distal end, prismatic guide member 104 is formed with a curved camming surface 108 (FIG. 12) which serves to bend web 100 during a distally directed motion thereof. A distal end portion 110 of web 102 emerges from an opening 112 at the distal end of prismatic guide member 104 as a result of the bending of web 102 by camming surface 108 a pushing of web 100. Web 100 is provided at its distal end with a linear cutting edge 114. Cutting edge 114 moves in a linear direction 116 in a plane (not designated) oriented transversely to tubular member 98.

As depicted in FIGS. 13A, 13B, and 13C, tubular member 98 may be provided with an obturator 118 slidably inserted in channel 106. During an initial step in a biopsy procedure (FIG. 13A), tubular member 98 is inserted together with obturator 118 through tissues (not shown) overlying the tissues of which a sample is desired. In occupying channel 106 during the initial step of the biopsy procedure, obturator 118 blocks insertion of the overlying tissues. Upon the arrival of the distal end of tubular member 98 at the region of underlying tissues, obturator 118 is withdrawn in the proximal direction (FIG. 13B), thereby opening a chamber 120 at the distal end of channel 106. Tubular member 98 is then inserted further into the patient so that a specimen of the underlying tissues enters chamber 120. Upon completion of this insertion (FIG. 13C), web 100 is pushed in the distal direction through channel 102 of prismatic member guide 104. Consequently, web 100 is bent at the distal end of channel 102 by camming surface 108 and cutting edge 114 is shifted in transverse direction 116 to sever a tissue specimen inserted into chamber 120.

Upon severing of the tissue specimen from the remaining organic tissues of the patient, tubular member 98 is withdrawn. Obturator 118 may then be used to push the tissue specimen from chamber 120 of tubular member 98 into a container (not shown).

Biopsy instrument assemblies as described herein may be inserted into leg ulcers and any kind of bony ulcer, as well as pressure ulcers, for example, in the hip or pelvis. The tubular members of the different embodiments can go through infected, fragile, frail old bone. To that end, the tubular members are preferably made of a strong metallic substance.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for use in obtaining a biopsy, comprising the steps of:
   providing an instrument assembly including an elongate tubular member having a longitudinal axis and a distal end portion defining a specimen-receiving chamber, said instrument assembly being provided with a rod extending along said axis and with a cutting blade connected to said rod at a distal end thereof and extending in a plane oriented substantially transversely with respect to said tubular member;
   inserting said distal end portion of said tubular member into organic tissues of a patient so that some of said tissues enter said chamber;
   upon sufficient insertion of said distal end portion of said tubular member into the organic tissues of the patient, rotating said rod to move said blade in said plane to thereby sever tissues in said chamber from tissues outside said chamber; and
   upon completion of said step of moving, removing said distal end portion of said tubular member, together with severed organic tissues captured in said chamber, from the patient.

2. The method defined in claim 1 wherein said blade is a linear blade extending diametrically across a distal end face of said tubular member, said step of moving including the step of rotating said blade in said plane.

3. The method defined in claim 1, further comprising the steps of pushing from said chamber the severed organic tissues captured in said chamber.

4. The method defined in claim 1 wherein said instrument assembly includes at least one culture medium in said tubular member, said step of inserting including the step of placing the organic tissues from the patient in contact with the culture medium.

5. An instrument assembly for use in obtaining a biopsy, comprising:
   an elongate tubular member defining a specimen-receiving chamber at a distal end, said tubular member having a longitudinal axis;
   a rod extending through said tubular member along said axis, said rod being rotatably coupled to said tubular member; and
   a cutting blade connected to said rod at a distal end thereof, said cutting blade having a cutting edge extending in a plane oriented transversely with respect to said tubular member, said cutting blade being operatively connected to said tubular member via said rod.

6. The instrument assembly defined in claim 5 wherein said blade is a linear blade extending diametrically across a distal end face of said tubular member, said blade being rotatably mounted to said tubular member for motion in said plane.

7. The instrument assembly defined in claim 5, further comprising at least one culture medium in said tubular member.

8. The instrument assembly defined in claim 5 wherein said tubular member is provided at said distal end with a sharp edge oriented distally for facilitating insertion of said tubular member into organic tissues a patient.

* * * * *

UNITED STATES PATENT AND TRADEMARK OFFICE
CERTIFICATE OF CORRECTION

PATENT NO. : 5,375,608
DATED : December 27, 1994
INVENTOR(S) : Jonathan Tiefenbrun and Peter J. Wilk It is certified that error appears in the above-indentified patent and that said Letters Patent is hereby corrected as shown below:

Column 3, line 21, insert --be-- after "may"; line 23, insert --of-- after "tissues".

Column 6, line 39, change "102" to --100--; line 41, change "102" to --100--; line 41, insert --and-- after "108".

Column 7, line 41, claim 1, change "moving" to --rotating--.

Column 8, line 5, claim 2, change "moving" to --rotating--; line 40, claim 8, insert --of-- after "tissues".

Signed and Sealed this

Sixteenth Day of May, 1995

Attest:

BRUCE LEHMAN

*Attesting Officer*     *Commissioner of Patents and Trademarks*